United States Patent [19]
Kriesel et al.

[11] Patent Number: 5,334,197
[45] Date of Patent: Aug. 2, 1994

[54] FLEXIBLE BASE FLUID DELIVERY APPARATUS

[75] Inventors: Marshall S. Kriesel, Saint Paul; Thomas N. Thompson, Richfield; Farhad Kazemzadeh, Bloomington, all of Minn.

[73] Assignee: Science Incorporated, Bloomington, Del.

[21] Appl. No.: 917,754

[22] Filed: Jul. 21, 1992

Related U.S. Application Data
[63] Continuation of Ser. No. 588,983, Sep. 25, 1990.

[51] Int. Cl.$^5$ .............................................. A61M 37/00
[52] U.S. Cl. ...................................... 604/132; 604/246
[58] Field of Search ............ 604/131, 132, 133, 890.1, 604/891.1, 892.1, 246, 247, 140–144, 212, 216, 217; 128/DIG. 12

Primary Examiner—C. Fred Rosenbaum
Assistant Examiner—Manuel Mendez
Attorney, Agent, or Firm—James E. Brunton

[57] ABSTRACT

An apparatus for the precise, ambulatory infusion of pharmaceutical fluids to a patient at controlled rates over extended periods of time of a character in which an elastic membrane cooperates with a thin, yieldably-deformable base to form a fluid chamber. When the base is deformed from a first configuration to a second configuration, internal stesses are formed within the membrane which causes it to tend to return toward its starting configuration and, in so doing, force fluid contained within the fluid chamber outwardly of the device through a fluid port.

19 Claims, 3 Drawing Sheets

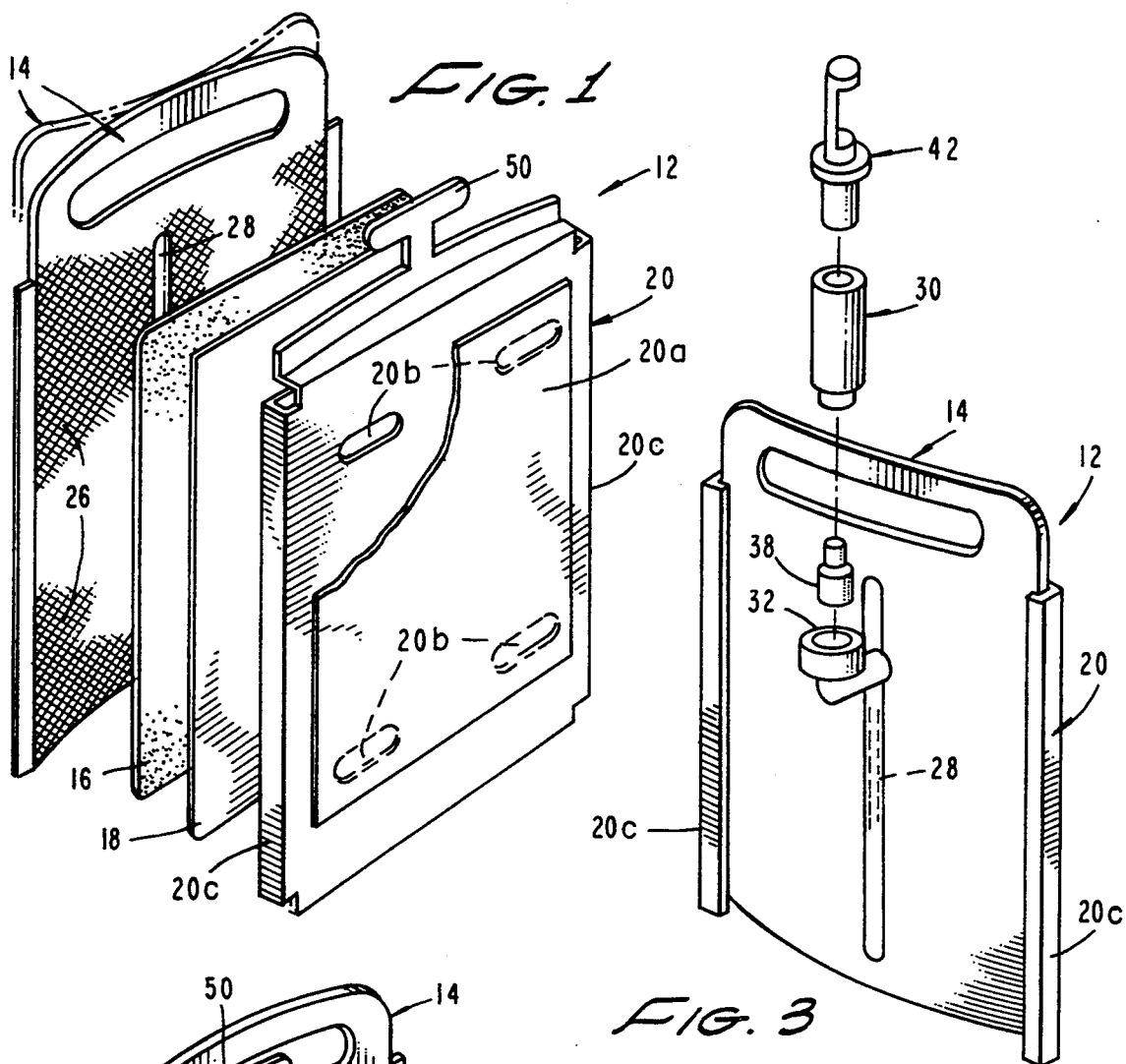
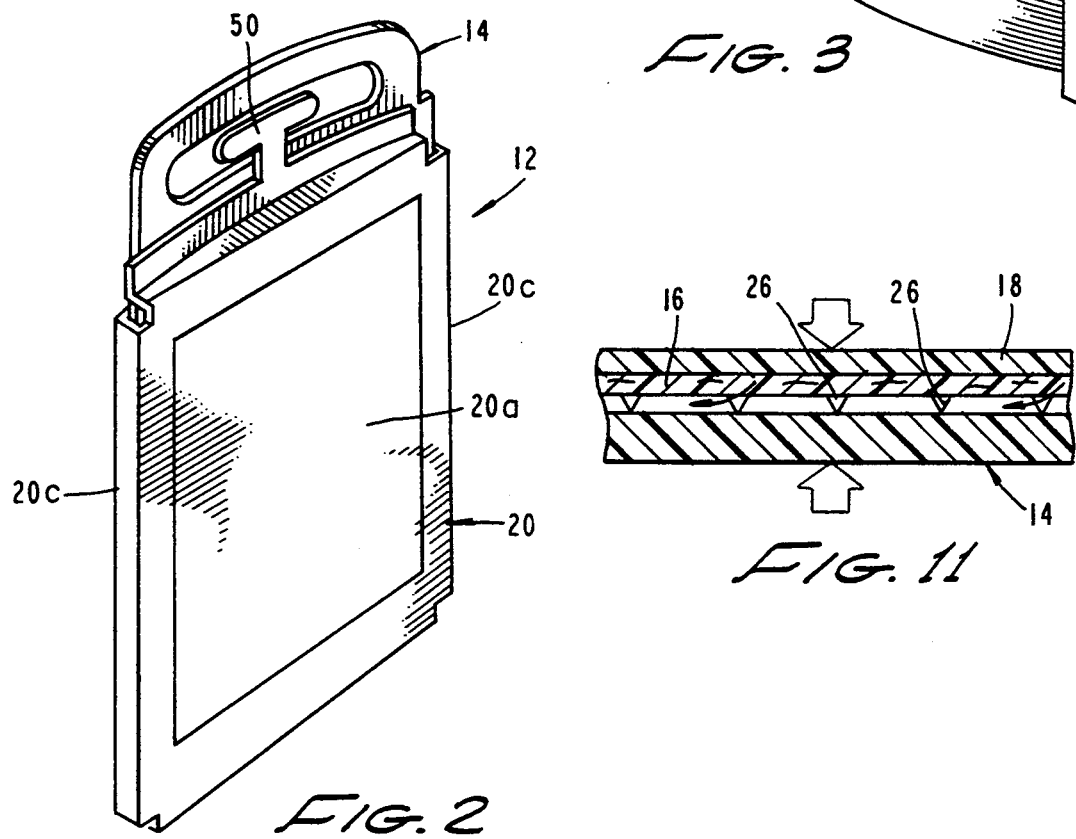

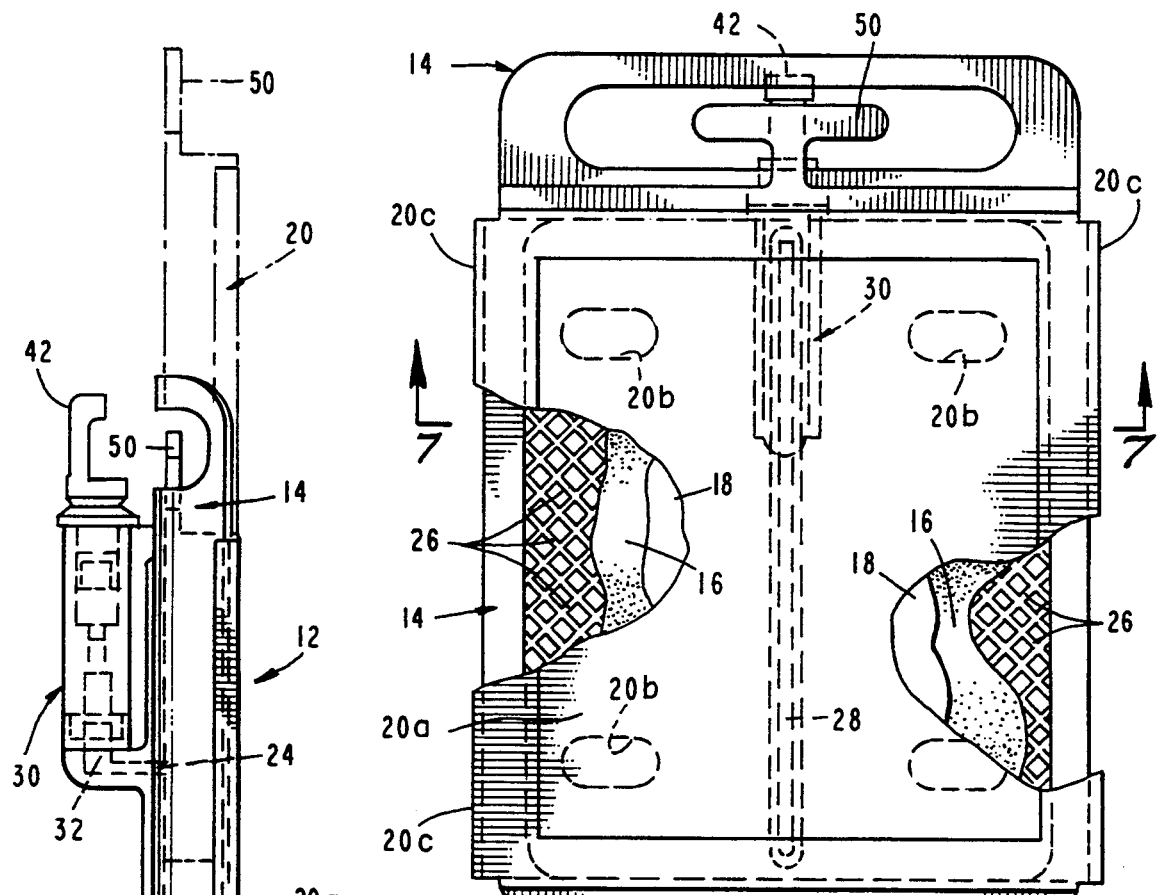
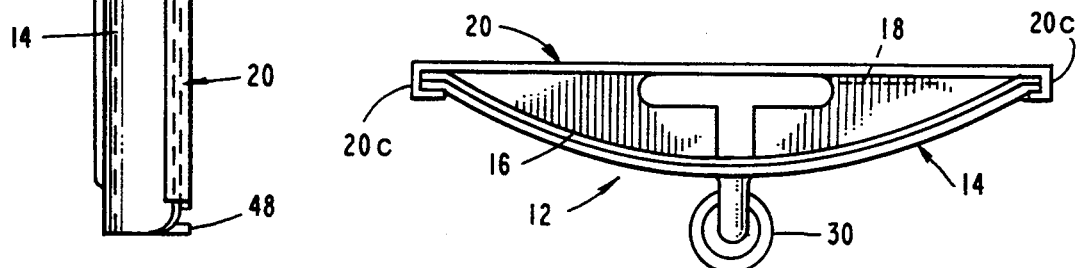
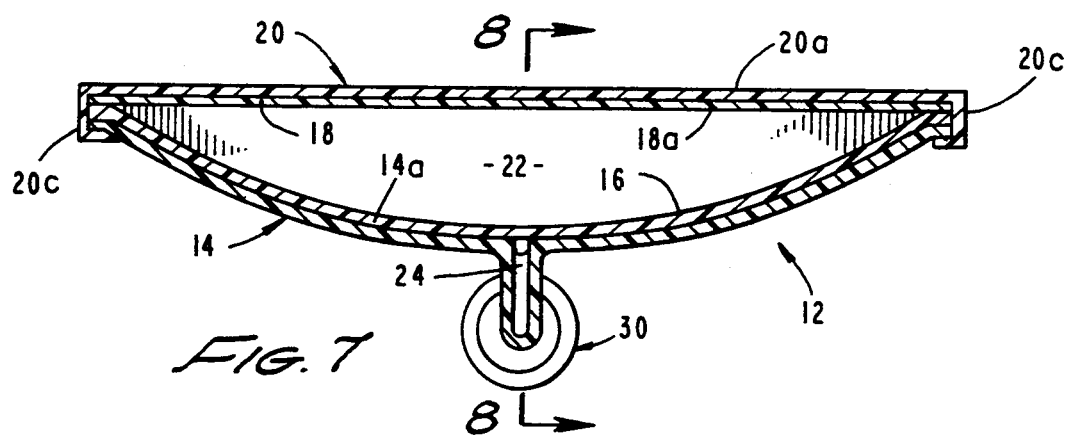

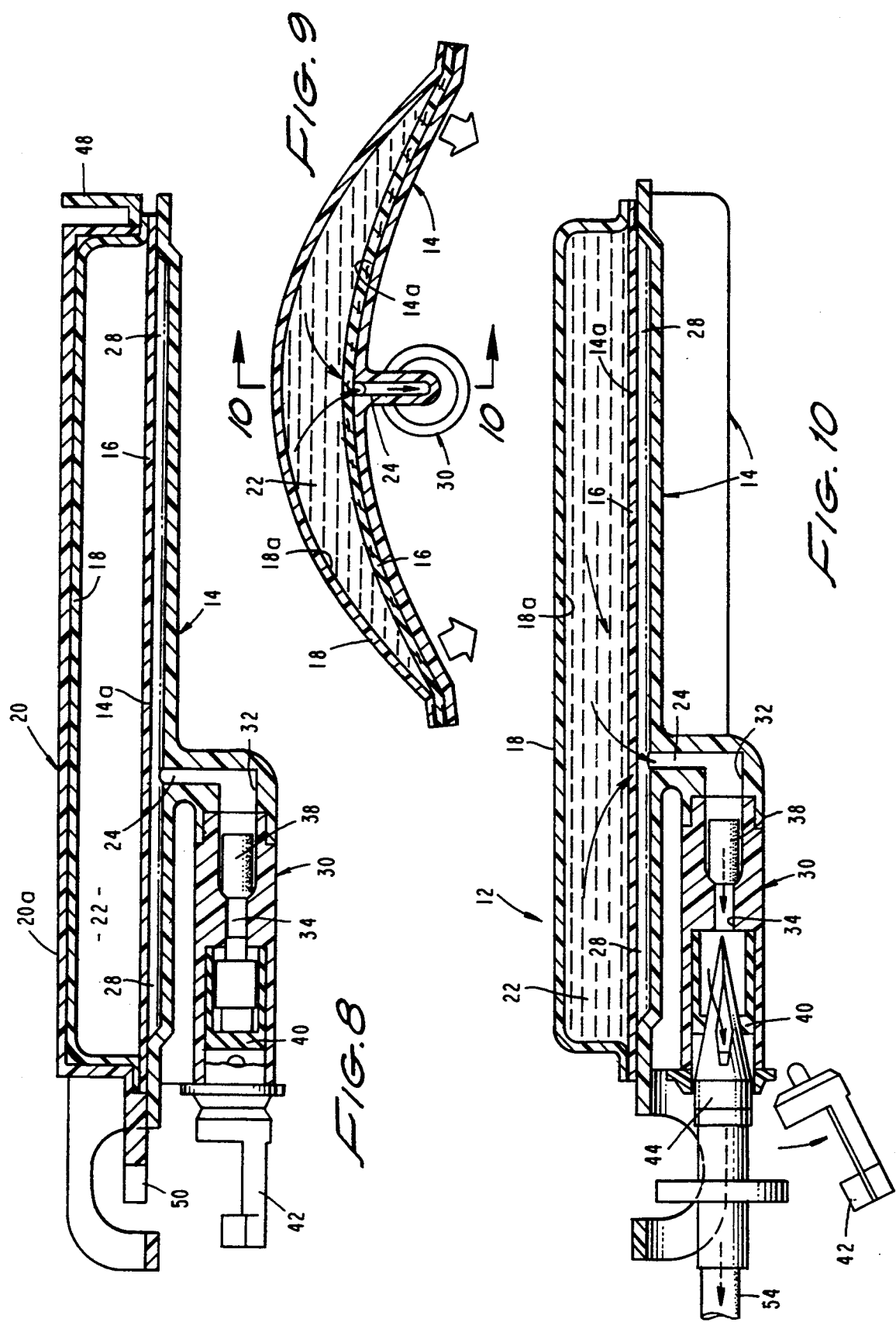

FLEXIBLE BASE FLUID DELIVERY APPARATUS

This is a continuation of application Ser. No. 07/588,983, filed Sep. 25, 1990.

BACKGROUND OF THE INVENTION

1. Field of the Invention

The present invention relates generally to fluid delivery devices. More particularly, the invention concerns an improved apparatus for ambulatory infusion of medicinal agents into a patient at specific rates over extended periods of time.

2. Discussion of the Invention

Many medicinal agents require an intravenous route for administration thus bypassing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished using gravity flow methods, which typically involve the use of intravenous administration sets and the familiar bottle or bag suspended above the patient. Such methods are cumbersome, imprecise and require bed confinement of the patient. Periodic monitoring of the apparatus by the nurse or doctor is required to detect malfunctions of the infusion apparatus and to control flow rate.

Devices from which liquid is expelled from a relatively thick-walled bladder by internal stresses within the distended bladder are well-known in the prior art. Such bladder, or "balloon" type, devices are described in U.S. Pat. No. 3,469,578, issued to Bierman and in U.S. Pat. No. 4,318,400, issued to Perry.

The prior art bladder type infusion devices are not without drawbacks. Generally, because of the very nature of bladder or "balloon" configuration, the devices are unwieldly and are difficult and expensive to manufacture and use. Further, the devices are somewhat unreliable and their fluid discharge rates are frequently imprecise and operate over a wide flow rate tolerance.

The apparatus of the present invention overcomes many of the drawbacks of the prior art by eliminating the bladder and making use of recently developed elastomeric membranes and new high performance engineering materials, which, in cooperation with a plate-like, yieldably deformable base define a fluid chamber that contains the fluid which is to be dispensed. Until the device is used, the elastomeric membrane is in a substantially relaxed state. However, movement of the yieldably deformable base from a first configuration, such as a concave configuration, into a second configuration, such as a convex configuration, imparts internal stresses to the elastomeric film membrane in a manner to cause the membrane to tend to move toward its starting configuration thereby controllably forcing fluid contained within the chamber into fluid flow channels provided in the base and then outwardly to the patient through a fluid outlet port in communication with the fluid chamber. In one form of the apparatus of the invention, a thin, planar shaped fluid interaction member, which may be a filter or a flow control member, is strategically located within the chamber to controllably act upon the fluid flowing toward the fluid flow channels.

The use of state of the art thin membranes and films permits the construction of compact, low profile, laminated structures which are easy to use and inexpensive to manufacture. When the devices of the invention are to be used with ambulatory patients they are constructed of light-weight flexible materials so that the device can be carried by the patient.

The apparatus of the invention can be used with minimal professional assistance in an alternate health care environment, such as the home. By way of example, devices of the invention can be used for the continuous infusion of antibiotics, hormones, steroids, anti-blood clotting agents, blood and blood components, blood substitutes analgesics, parenteral agents, enteralnasogastric feeding and delivery of other medical agents. Similarly, the devices can be used for extended I-V micro infusion such as chemotherapy and KVO (keep vein open) and can accurately deliver fluids to the patient in precisely the correct quantities and at extended microfusion rates over time.

SUMMARY OF THE INVENTION

It is an object of the present invention to provide an apparatus for expelling fluids at a precisely controlled rate which is of a compact, low profile, laminate construction. More particularly, it is an object of the invention to provide such an apparatus which can be used for the precise infusion of pharmaceutical fluids to an ambulatory patient at controlled rates over extended periods of time.

It is another object of the invention to provide an apparatus of the aforementioned character in which an elastic membrane cooperates with a thin, yieldably deformable base to form a fluid chamber. When the base is deformed from a first configuration to a second configuration, internal stresses are formed within the membrane which causes it to tend to return toward its starting configuration and in so doing force fluids contained within the fluid chamber outwardly of the device through a fluid port.

Another object of the invention is to provide a device in which the yieldable base and the distendable membrane cooperate to form an optimized stored energy source for dispelling fluid from the fluid chamber.

Another object of the invention is to provide a device as described in the preceding paragraph in which the distendable membrane, which acts as the energy source for dispelling fluid from the device, is maintained in a substantially relaxed, unstressed state, until the device is to be used.

Another object of the invention is to provide a disposable device of the class described which is highly reliable and easy-to-use by lay persons in a non-hospital environment.

Another object of the invention is to provide an apparatus which can be factory prefilled with a wide variety of medicinal fluids, or one which can readily be filled in the field shortly prior to use.

Another object of the invention is to provide an infusion device which is operational in all altitudes and attitudes at a wide range of temperatures.

A further object of the invention is to provide a low profile, fluid delivery device of laminate construction which can be manufactured inexpensively in large volume by automated machinery.

Another object of the invention is to provide an apparatus of the aforementioned character in which the distendable membrane is permeable to gases at least in one direction.

Another object of the invention is to provide a fluid delivery device embodying an iostropic distendable membrane with a uniform modulus of elasticity which cooperates with a base to define a fluid chamber having a fluid outlet in communication with a fluid passageway provided within a fill assembly which includes a valve element disposed within the fluid passageway to control fluid flow there through.

A further object of the invention is to provide a fluid delivery device embodying a distendable membrane assembly which cooperates with a base to define a fluid chamber having a fluid outlet in which the distendable membrane assembly is of multilaminate construction being made up of a plurality of individual members or layers which cooperate to controllably urge fluid within the fluid chamber outwardly of the fluid outlet of the device. Additionally, the multilaminate composite can function to provide directional gas migration control and to provide a fluid chamber membrane interfacial, bio-chemical surface.

Another object of the invention is to provide a fluid delivery device of the character described in the preceding paragraph in which the base is provided with a multiplicity of micro-channels for conducting fluid toward the fluid port of the device at a precise rate.

Yet another object of the invention is to provide a delivery device of the class described in which the deformable geometry creates a positive ullage configuration to ensure maximum positive expulsion of fluid from the fluid chamber.

BRIEF DESCRIPTION OF THE DRAWINGS

FIG. 1 is an exploded, generally perspective view of one form of the fluid delivery apparatus of the present invention.

FIG. 2 is a generally perspective, front view of the apparatus of FIG. 1 as it appears in an assembled configuration.

FIG. 3 is a generally perspective, rear view of the apparatus of the invention.

FIG. 4 is an enlarged side elevational view of the apparatus.

FIG. 5 is a top plan view of the apparatus partly broken away to show internal construction.

FIG. 6 is an end view of the apparatus.

FIG. 7 is a cross-sectional view taken along lines 7—7 of FIG. 5.

FIG. 8 is a cross-sectional view taken along lines 8—8 of FIG. 7.

FIG. 9 is a cross-sectional view of the apparatus similar to FIG. 7, but showing the apparatus with the slidable cover removed and the base moved into a second position to impart internal stresses to the distendable membrane of the device.

FIG. 10 is a cross-sectional view taken along lines 10—10 of FIG. 9.

FIG. 11 is an enlarged, fragmentary, cross-sectional view of a portion of the base and fluid interaction element of the apparatus illustrating the flow of fluid through microchannels provided in the base portion of the apparatus.

DESCRIPTION OF THE INVENTION

Referring to the drawings and particularly to FIGS. 1, 2, and 3, the device of the present invention for expelling fluids at a controlled rate is generally designated by the numeral 12. This embodiment of the invention comprises a yieldably deformable base 14; fluid interaction means, shown as a thin membrane 16, connected to base 14; means for forming a fluid chamber, shown as a distendable membrane 18 overlaying and terminally secured to member 16 and to base 14; and securement means, shown as a removable cover 20 which is slidably connected to base 14.

As best seen by referring to FIGS. 7 and 9, base 14 is yieldably deformable from a first position shown in FIG. 7, wherein the first surface 14a of base 14 is in a first configuration, namely a concave configuration, to a second position, shown in FIG. 9, wherein first surface 14a is in a second configuration, namely a convex configuration. Movement of base 14 from the first configuration to the second configuration is accomplished in a manner presently to be described after slidably removable cover 20 has been separated from base 14.

When base 14 is in the first position shown in FIG. 7, distendable membrane 18 is in a substantially unstressed, planar configuration with the first surface 18a thereof being disposed in a first position relative to the first surface 14a of base 14. However, when base 14 is moved into the second position shown in FIG. 9, membrane 18 is distended so that the first surface 18a thereof is disposed in a second position relative to first surface 14a of base 14. As will be discussed further hereinafter, when base 14 is in the second position shown in FIG. 9, internal stresses are imparted to membrane 18 which will tend to return the membrane toward its less distended, starting configuration. As membrane 18 moves toward its starting configuration, fluid contained within a chamber 22 which is formed between membrane 18 and base 14, will be urged from the chamber through a fluid outlet port 24. For certain end uses of the device, it may be desirable to construct membrane 18 from a gas permeable material so that gases can be controllably vented from chamber 22.

Referring now to FIGS. 5 and 11, it is to be noted that first surface 14a of base 14 is provided with a multiplicity of crossing microflow channels 26 which communicate with a longitudinally extending fluid-flow passageway 28 which, in turn, is in communication with an outlet port 24. As distendable membrane 18 tends to return to its normal, less distended configuration, fluid will be forced through the fluid interaction means, or membrane 16, through the microchannels 26, toward longitudinally extending fluid channel 28 and then outwardly of the device via outlet port 24.

Interconnected with base 14 is accessing means for accessing chamber 22 to either fill it with fluid or to controllably dispense fluid therefrom. In the form of the invention here shown, the accessing means comprises an accessing assembly including an elongated body 30 having a fluid passageway 32 therethrough. One end of passageway 32 is in communication with port 24 and the other is in communication with a fluid dispensing port 34. For certain applications, a check valve 38 may be provided within passageway 32 to control the direction of fluid flow therethrough. For example, in factory prefilled devices, the check valve may permit fluid flow only in the direction of the dispensing port of the device.

Disposed within body 30 is a septum 40 which normally closes the previously mentioned dispensing port 34 relative to atmosphere. Septum 40 is constructed of a soft rubber or plastic material adapted to sealably receive penetrating means such as an I-V administration set spike, hollow needle or a cannula of the character used to access passageway 32. With this construction, chamber 22 can either be filled with fluid at the time the device is manufactured and prior to assembly of the septum and the body, or alternatively, chamber 22 can be filled with fluid in the field using an appropriate filling means.

To maintain the septum in a sterile condition, a tear-away cap 42 is connected to body 30 as indicated in FIG. 8. Prior to using the device cap 42 is removed in the manner shown in FIG. 10 so that sterile access to septum 40 can be achieved by a penetrating member such an I-V administration set spike shown as member 44 FIG. 10.

As best seen in FIGS. 1, 2, and 7, slidable cover 20 is provided with a planar wall 20a having vent apertures 20b and side portions 20c which are grooved to closely accept the edges of the assembly made up of base 14 and membranes 16 and 18. As indicated in FIG. 8, cover 20 also includes a tear-away tab or wall 48 which must be removed before cover 20 can be slidably removed in the manner shown by the phantom lines in FIG. 4. To assist in slidably removing the cover, a gripping member 50 is provided on the end of the cover opposite locking tab 48.

In using the apparatus of the invention, if the reservoir 22 is not filled at the time of manufacture, tear-off cover 42 is removed and the appropriate fluid is injected into chamber 22 using appropriate filling means via septum 40. On the other hand, if chamber 22 has been filled with fluid at the time of manufacturing the device, tab 48 on cover 20 is removed so that the cover can be slidably removed from the base and membrane assembly portion of the device in the manner shown by the phantom lines in FIG. 4. Gripping means, or handle 50, is conveniently used to accomplish this step. Once the cover 20 has been removed, the base membrane subassembly has the general configuration shown in FIG. 9 that is with surface 14a and base 14 in a generally convex orientation. It is to be understood that base 14 is molded so that upon removal of the cover member, the base can readily be moved into the second position shown in FIG. 9. In a manner well understood by those skilled in the art, base 14 can be constructed with internal stresses embodied therein tending to cause it to automatically snap into the second configuration upon removal of cover 20. Alternatively base 14 can be constructed so that it is substantially unstressed and can be deformed into the second configuration only upon exertion of a manual force. As previously mentioned, as the base moves from the first to the second configuration, internal stresses will be created in membrane 18 which tend to continuously cause the membrane to move toward its original, less stressed configuration. As the membrane tends to move toward its starting configuration, fluid will be controllably forced through fluid interaction means or membrane 16 into the multiplicity of microchannels 26, then into elongated channel 28 and finally through port 24. Fluid flowing through port 24 will pass through the check valve 38 through port 34 and into the penetrating means 44. Means 44 is connected with the patient by any suitable conduit such as tubing 54. (FIG. 10). When base 14 is constructed in a prestressed state, it will cooperate with distendable membrane 18 to form an optimized stored energy source for dispelling fluids from the fluid chamber. In this way, substantial reduction in the elongation of the distendable membrane is compensated through the additional loading provided by the prestressed base.

The state of the art materials used in the construction of the apparatus of the invention markedly contribute to the reliability, accuracy and manufacturability of the apparatus. A brief review of these materials follows:

With respect to the base 14, a wide variety of materials can be used, including; metals, rubber or plastics that are compatible with the liquids they contact. Examples of such materials and composites are stainless steel, aluminum, latex rubber, butyl rubber, nitrile rubber, polyisiprene, styrene-butadiene copolymer, silicones, polyolefins such as polypropylene and polyethylene, polyesters, polyurethane, polyamides and polycarbonates. Manufacturers of suitable materials include; Dow Corning of Midland, Mich., General Electric of Schenectady, N.Y. and Shell Chemical Company of Houston, Tex., DuPont Chemical of Wilmington, Del., and Eastman Chemical of Kingsport, Tenn.

Considering next the fluid interaction means, or member 16, and this important component can take the form of a filter or a flow control means. Precision microflow through the membrane can be a controlled flow delivery process with controllable delivery rates being between 0.1 to 4.5 milliliters per hour. Depending on the medicinal agent to be delivered and the required flow rate regime, several microporous membranes can be employed for such rate control, including asymmetric substrate based films such as cellulose acetate, cellulose acetate buterate, and ethyl cellulose. These membrane films may vary from 20 microns to 100 microns thick and can be made of a porous substrate with a controlled skin where the active porosity can vary from angstroms to 50 microns in diameter. Additionally, other acrylic resins can also be used for thin film, delivery membranes such as polymethyl-methacrylate (PMM) and polysulfone on PVC also with approximately 2 microns thickness of skin of active membrane surface on up to 100 microns of substrate backing. Other matrix polymer systems are also candidates for microfilm membranes and include PCCE copolyesters and nylon PEBAX-polyethersteramide (PEEA), as well as PTFE, PVDF, P-P mixed ester cellulose and certain other polycarbonates. Manufacturers of these materials include; Bend Research (Cellulose Acetates, polysulfones), Eastman Chemical (PCCE Copolyester #9966), Atochem (PEBAX Nylon), Dupont (Hytrel), Rohm Pharmaceuticals (Acrylic Resins) and Millipore (PTFE), PVDF and mixed ester cellulose).

Considering next the elastic distendable membrane 18, this important component can be manufactured from several alternate materials including rubbers, plastics and other thermoplastic elastomers. These include latex rubber, polyisoprene (natural rubber), butyl rubber, nitrile rubber, fluroelastomers, flurosilicone elastomers and other elastomers of homopolymer, copolymers (random, alternating, block, graft, crosslink and starblock), mechanical poly-blends and interpenetrating polymer network composition.

Examples of materials found particularly well suited for this application include; silicone polymers (polysiloxanes) (high performance silicone elastomers made from high molecular weight polymers with appropriate fillers added. These materials are castable into thin film membrances and have high permeability (which allows maximum transport of vapor and gas), high bond and tear strength and excellent low temperature flexibility and radiation resistance. Additionally, silicone elastomers retain their properties over a wide range of temperature ($-80°$ to $200°$ C.) are stable at high temperatures, and exhibit tensile strengths up to 2,000 lb./in$^2$ elongation up to 600%.

Further, silicone (polyorganosiloxanes) are thermally stable, hydrophobic organometallic polymers with the lowest P-P interaction (of all commercially available polymers. This fact coupled with the flexibility of the backbone results in a low Tg ($-80°$ C.) and an amorphous rubbery structure for the high MW (polydimethylsiloxanes). Silicone rubber membranes are considerably more permeable to gases than membranes of any other polymer. Depending on the medicinal fluid used and the filling of the storage mode, which will determine the desired mass transport characteristics of the membrane (permeability and selectivity), other materials of choice include polyurethanepolysiloxane copolymers, blends and IPN's. By example, polydimethylsiloxane (PDMS) and polyurethane (PU) multicomponent IPN containing 10%–20% weight of PU shows enhanced initial modulus relative to that of PDMS itself.

Interpenetrating polymer networks (IPNS) are unique blends of cross-linked polymers containing essentially no covalent bonds, or grafts between them. True IPNS are also homogeneous mixtures of component polymers. Further examples of an additional candidate materials would be a polyurethanepolysiloxane (IPN) bilaminated with a polyparaxylene or alternately bilamination of polydimethylsiloxane (PDMS) and polyparaxylene. Coextruded laminates of this type can be selected according to the desired gas permeability for vapor and $O_2$, $N_2$ and $CO_2$ diffusion and their specific selectivity requirements as well as for direction of gas migration when appropriately layered and when the end user of the device makes gas migration appropriate. As previously mentioned, member 18 can be constructed from a single, thin sheet or it may be of multilaminate construction.

Manufacturers of materials suitable for use in the construction of the distendable membrane, include Dow Chemical, 3M Company, General Electric, B.P. Polymers, Mobay Chemical, Shell Oil Corp., Petrarch Systems, DuPont, Concept Polymers and Union Carbide Corp.

With respect to the slidable cover 20, this component can be produced from one of several polymer groups. The material selected is preferably strong, lightweight, has a high degree of chemical resistance and depending on the particular configuration of the apparatus, can be flexible. Depending on the particular application of the device, the following polymers can be employed: Polypropylene(PP), Ultra high molecular weight polyethylene (UHMW PE), High density polyethylene (HDPE), Polyvinylidene Fluoride (PVDF), Ethylene-vinyl acetate (EVA), Styrene Acrylonitrile (SAN), Polytetrafluoroethylene (PTFE) nylon, polycarbonate, polystyrene and polysulfone. A suitable source of these materials is Porex Technologies of Fairburn, Ga.

Having now described the invention in detail in accordance with the requirements of the patent statutes, those skilled in the art will have no difficulty in making changes and modifications in the individual parts or their relative assembly in order to meet specific requirements or conditions. Such changes and modifications may be made without department from the scope and spirit of the invention, as set forth in the following claims.

I claim:

1. A device for expelling fluids at a controlled rate, comprising:
   (a) a yieldably deformable solid base having first and second surfaces, said solid base being deformable from a first position wherein said first surface is in a first configuration to a second position wherein said first surface is in a second configuration;
   (b) means for forming a fluid chamber comprising a distendable membrane having a first surface and being constructed of an elastic material, said first surface of said membrane being disposed in a first position relative said first surface of said solid base when said base is in said first position and being disposed in a second position relative said first surface of said solid base when said base is in said second position to form a fluid chamber between said first surface of said solid base and said first surface of said membrane said fluid chamber having a fluid port, said distendable membrane being distendable when said solid base is in said second position in a manner to establish internal stresses therewithin tending to return said membrane to a less distended configuration whereby fluid within said chamber will be urged to flow from said fluid port; and
   (c) means removably connected to said solid base for maintaining said base in said first position.

2. A device as defined in claim 1 in which said base, upon being deformed into said second position, tends to return to said first position.

3. A device as defined in claim 2 further including fluid interaction means disposed intermediate said base and said distendable membrane for acting upon fluid flowing from said fluid chamber toward said fluid port.

4. A device as defined in claim 3 in which said fluid interaction means comprises a filter for filtering fluid flowing toward said fluid port.

5. A device as defined in claim 3 in which said fluid interaction means comprises a microporous membrane.

6. A device for expelling fluids at a controlled rate, comprising:
   (a) a yieldably deformable base having first and second surfaces, said base being deformable from a first position wherein said first surface is in a first generally concave configuration to a second position wherein said first surface is in a second generally convex configuration; and
   (b) means for forming a fluid chamber comprising a distendable membrane having a first surface and being constructed of an elastic material, said first surface of said membrane being disposed in a first position relative said first surface of said base when said base is in said first position and being moved into a second position relative said first surface of said base when said base is in said second position to form a fluid chamber between said first surface of said base and said first surface of said membrane, said fluid chamber having a fluid port, said distendable membrane being distendable when said base is in said second position in a manner to establish internal stresses therewithin tending to return said membrane to a less distended configuration whereby fluid within said chamber will be urged to flow from said fluid port.

7. A device as defined in claim 6 further including securement means removably connected to said base for maintaining sad base in said first position.

8. A device as defined in claim 6 in which said first surface of said base is provided with at least one fluid flow channel in communication with said fluid port.

9. A device as defined in claim 8 further including fluid interaction means superimposed over said fluid flow channel for acting upon fluid flowing from said fluid chamber toward said fluid flow channel.

10. A device as defined in claim 8 in which said membrane is gas permeable.

11. A device as defined in claim 8 further including accessing means in communication with said fluid port for filing said chamber with fluid and for dispensing fluid therefrom.

12. A device as defined in claim 11 in which said accessing means comprises a fill assembly comprising:
(a) a body having a fluid passageway in communication at one end with said fluid port; and
(b) valve means disposed within said fluid passageway for regulating fluid flow through said passageway.

13. A device as defined in claim 12 in which said securement means comprises a cover membrane slidably connected to said base.

14. A device as defined in claim 13 in which said cover member is provided with vent means for venting gases disposed intermediate said cover member and said membrane.

15. A device for expelling fluids at a controlled rate, comprising:
(a) a yieldably deformable base having first and second surfaces, said base being deformable from a first position wherein said first surface is a first configuration to a second position wherein said first surface is in a second configuration;
(b) means for forming a fluid chamber comprising a distendable membrane having a central portion and marginal portions circumscribing said central portion, said marginal portions of said membrane being connected to said first surface of said base with said central portion of said membrane being disposed in a first position relative said first surface of said base when said base is in said first position and being moved into a second position relative said first surface of said base when said base is deformed into said second position to form a fluid chamber between said first surface of said base and said central portion of said membrane, said chamber having a fluid port, said distendable membrane being substantially unstressed when said base is in said first position and being internally stressed when said base is in said second position in a manner tending to return said membrane to its substantially unstressed condition, whereby fluid within said chamber will be urged to flow from said fluid port.

16. A device as defined in claim 15 further including means removably connected to said base for maintaining said base in said first position.

17. A device as defined in claim 15 further including fluid interaction means disposed intermediate said base and said distendable membrane for acting upon fluid flowing from said fluid chamber toward said fluid port.

18. A device as defined in claim 15 further including accessing means in communication with said fluid port for filling said chamber with fluid and for dispensing fluid therefrom.

19. A device as defined in claim 15 in which said accessing means comprises a septum penetrable by an I-V administration set spike.

* * * * *